United States Patent [19]

Cho

[11] 4,257,411

[45] Mar. 24, 1981

[54] CRUCIATE LIGAMENT SURGICAL DRILL GUIDE

[76] Inventor: Kenneth O. Cho, 1234 - 19th St. N.W., Washington, D.C. 20036

[21] Appl. No.: 10,197

[22] Filed: Feb. 8, 1979

[51] Int. Cl.³ .............................................. A61F 5/04
[52] U.S. Cl. ........................... 128/92 EB; 128/92 EA
[58] Field of Search ........ 128/92 EB, 92 EA, 92 CA, 128/83, 92 E

[56] References Cited

U.S. PATENT DOCUMENTS

| | | | |
|---|---|---|---|
| D. 245,918 | 1/1977 | Shen | D24/26 |
| 2,267,157 | 10/1941 | Lippincott | 128/83 |
| 3,814,089 | 6/1974 | Deyerle | 128/92 EB |
| 3,835,849 | 9/1974 | McGuire | 128/92 EB |
| 3,892,232 | 6/1975 | Neufeld | 128/92 EB |
| 3,896,500 | 7/1975 | Rambert et al. | 3/1 |
| 3,927,423 | 12/1975 | Swanson | 3/1.91 |
| 3,945,377 | 3/1976 | Kronner | 128/92 EB |
| 3,949,428 | 4/1976 | Cavandish et al. | 128/92 EB |
| 3,953,896 | 5/1976 | Treace | 3/1 |
| 3,953,899 | 5/1976 | Chamley | 3/1.911 |
| 3,961,854 | 6/1976 | Jaguet | 403/59 |
| 3,964,106 | 6/1976 | Huttler, Jr. et al. | 3/1.911 |
| 3,988,783 | 11/1976 | Treace | 3/1 |
| 4,159,716 | 12/1979 | Borchers | 128/92 EB |

FOREIGN PATENT DOCUMENTS

| | | | |
|---|---|---|---|
| 168885 | 5/1951 | Austria | 128/92 EB |
| 743492 | 10/1933 | France | 128/92 EA |
| 1287437 | 6/1972 | United Kingdom | 128/92 EA |
| 1448111 | 7/1976 | United Kingdom | 128/92 EB |
| 186084 | 3/1966 | U.S.S.R. | 128/92 EB |
| 583797 | 4/1977 | U.S.S.R. | 128/83 |

OTHER PUBLICATIONS

British J. of Surg., vol. VII, 1920, "The Crutial Lig. of the Knee Joint", Groves.
J. of Bone & Joint Surg., vol. 57A, pp. 608, 612, 1975. Cho. "Reconstruction-Anterior Cruciate Lig., by Semitendinous Tenodesis".
Clinical Ortho. & Related Research, #106, Jan. Feb. 1975, Girgis et al., "Cruciate Lig. of Knee Joint".
British J. of Bone & Joint Surg., vol. 51B, No. 1, Feb. 1969, pp. 135-139. Cess et al., "A Drilling Jig for Arthirodesis of the Hip".
"Academie de Chirurgie", May 12, 1937, pp. 640-641.

*Primary Examiner*—Robert W. Michell
*Assistant Examiner*—C. W. Shedd
*Attorney, Agent, or Firm*—David H. Semmes; Warren E. Olsen

[57] ABSTRACT

A surgical drill guide tool adapted to be temporarily mounted about a distal portion of the femur for drilling a bony tunnel through a portion of the femur, in a precise manner. The surgical tool allows very efficient location of the drill exit within the intercondylar notch, and exact drill exit location is very critical in reconstruction of the anterior cruciate ligament of the knee, for example. The surgical tool drill guide is characterized by having a first and second upright, with first and second drill sheaths located at their respective distal ends wherein transverse mounting means are provided to allow the surgeon to position the first and second drill sheaths tightly against opposite surfaces of the femur, for example, to provide a continuing and exact alignment for the drilling of the bony tunnel. The drill sheath at the distal end of the second upright is configured to fit inside the intercondylar notch, and allow exact placement of the exit of a bony tunnel which is drilled extra-articularly through the skin, and through the lateral femoral condyle, for example.

4 Claims, 1 Drawing Figure

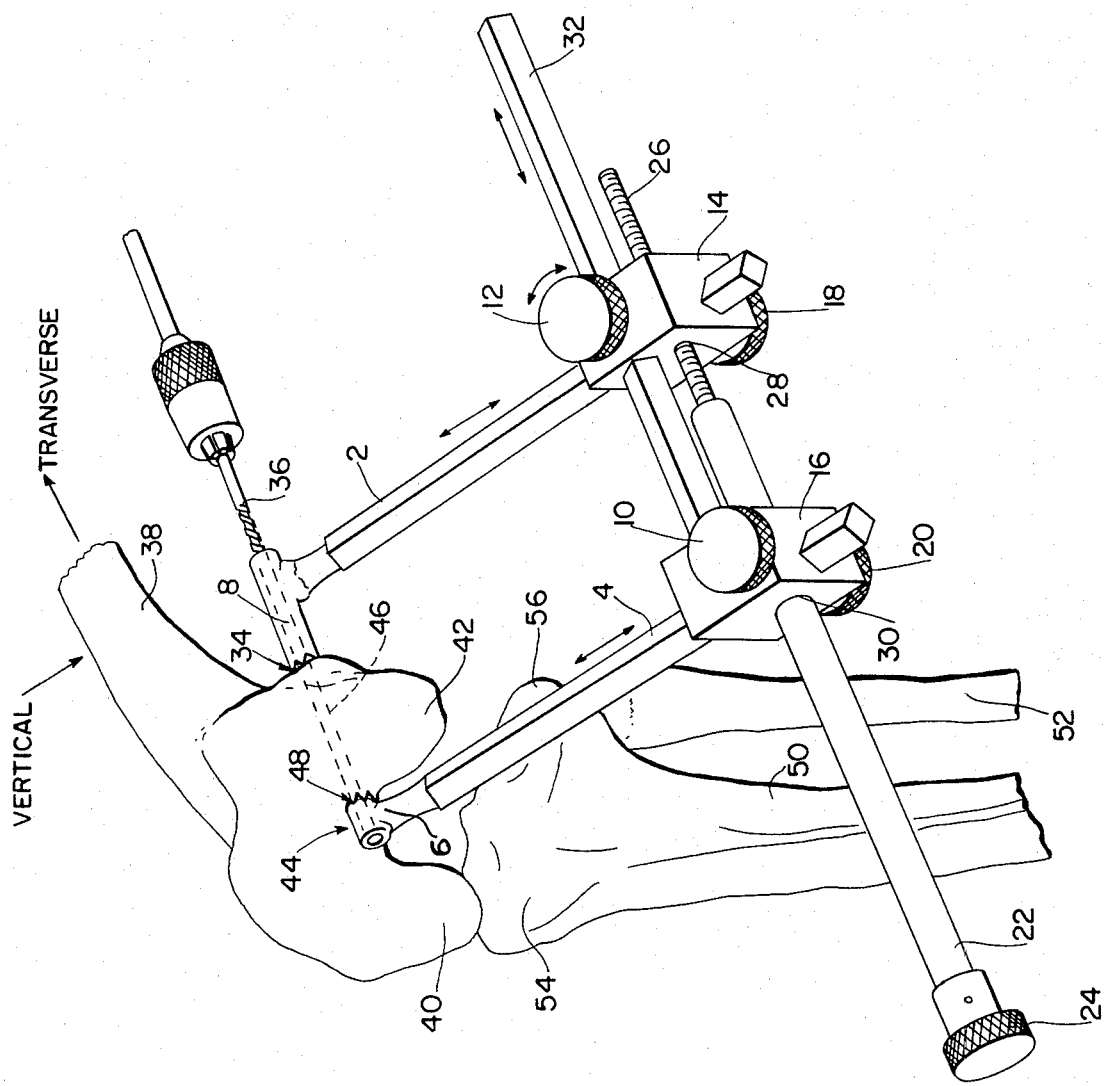

CRUCIATE LIGAMENT SURGICAL DRILL GUIDE

BACKGROUND OF THE INVENTION

1. Field of the Invention

The present invention is a surgical tool, particularly a drill guide for knee surgery. Exactly locating the exit of a bony tunnel is necessarily a critical part in certain surgical techniques, and particularly the reconstruction of the anterior cruciate ligaments by semitendenosis tenodesis, as previously taught by applicant. See Cho, Kenneth: *Reconstruction of the Anterior Cruciate Ligament by Semitendonosis Tenodesis.* J. Bone and Joint Surg., 57-A: 608–612, July 1975. As I noted in this paper, there are various surgical techniques for repairing——and even for reconstructing—cruciate ligaments of the knee. The present invention is most helpful with my technique, since it allows quick and accurate location of the exit point of a bony tunnel proximate the former femoral attachment location of a separated anterior cruciate ligament.

For more background upon the anatomy and problems of the anterior cruciate ligament, particular attention is drawn to Girgis, et al., *The Cruciate Ligaments of the Knee Joint, Anatomical Funcation and Experimental Analysis,* Clinical Orthopedics 106: 216–231, January-February 1975. Another surgical technique which also lends itself to use of the instant surgical tool is that taught by Hay-Groves, *The Crucial Ligaments of the Knee Joint: Their Function, Rupture, and Operative Treatment of the Same.* British J. Surg. Volume VII, 505–515 (1920). To the applicant's knowledge, the only type of cruciate ligament guide available is the Marcus Stewart cruciate ligament guide, which is primarily for the reattachment of a repairable torn anterior cruciate ligament to its original femoral insertion. See Stewart, M.J.: Campbell's Operative Orthopedics, 5th Edition, page. 929.

2. Description of the Prior Art

Within the general field of orthopedic surgery, there exist a number of drill guides, specifically sized and configured for particular purposes. However, and as previously noted, there is not available a guide which allows particular location of a bony tunnel through the distal end of the femur, as it is particularly necessary for my above-noted technique for reconstructing an anterior cruciate ligament, and particularly by means of using the semitendinosus tenodesis to recreate the function formally performed by the separated anterior cruciate ligament. This technique requires a hole approximately 0.64 cm. in diameter to be exactly located on a surface of the intercondylar notch. Prior to the present invention, this femoral hole was drilled toward the femoral intercondylar notch by rough alignment with a guide wire which was placed at the femoral insertion of the anterior cruciate ligament, to give a measure of orientation.

While drill guides for a specific orthopedic procedure are generally known, particularly for total hip replacements, there is not found in the prior art a device which would accommodate the special needs of an accurately located exit hole in the intercondylar notch of a femur, as required according to both my procedure and other knee reconstructive procedures which were noted above. Prior art patents known to applicant are, as follows:

Great Britain Pat. No. 1,448,111
Shen Des. No. 245,918
Schultz U.S. Pat. No. 3,727,611
Deyerle U.S. Pat. No. 3,814,089
McGuire U.S. Pat. No. 3,835,489
Neufeld U.S. Pat No. 3,892,232
Rambert, et al. U.S. Pat. No. 3,896,500
Swanson U.S. Pat. No. 3,927,423
Kronner U.S. Pat. No. 3,945,377
Cavendish, et al. U.S. Pat. No. 3,949,428
Treace U.S. Pat. No. 3,953,896
Charnley U.S. Pat. No. 3,953,899
Jaquet U.S. Pat. No. 3,961,854
Hutter, et al. U.S. Pat. No. 3,964,106
Treace U.S. Pat. No. 3,988,783

These patents illustrate various and sundry drill guides and clamps, for particular applications, such as repairing fractures of the femur or aiding an implantation, such as a total knee prosthesis. Firstly, it is noted that of the above-noted patents, several relate to specific orthopedic modifications of the knee joint.

Cavendish teaches a total knee prosthesis, together with an implantation jig adapted for connection to the femur, in order to locate his prosthetic components with respect to the natural condyles of the femur. As Cavendish shows in FIGS. 3 and 4, and discusses at column 4, lines 50+, his jig includes tubes which act as drill guides for placing certain pins directly into the femur. Cavendish, however, does not address the structurally unrelated problem of reconstructing a cruciate ligament.

Treace U.S. Pat. No. 3,953,896 illustrates one type of prosthetic ligament, and particularly an artificial ligament which has utility for replacing a damaged cruciate ligament. Treace is considered to be merely of interest, since he does not illustrate any device to locate the "natural points" of attachment for his ligament prosthesis. Treace U.S. Pat. No. 3,988,783 illustrates another artificial reconstruction for the knee, with particular focus upon the collateral ligaments.

Rambert, et al. illustrate a ligament reconstruction wherein strands of a polyamide material are encased in a polymer sheath. While Rambert's technique also requires tunnels, 26 and 27, to be bored into the distal end of the femur, there is no particular teaching of a device to ensure the accurate location of such tunnels.

The patents to Swanson, Charnley, and Hutter, et al. simply illustrate further surgical approaches to knee reconstructions, and particularly total knee reconstructions. As such, they are not particularly pertinent to the new device taught herein. For example, Swanson illustrates a patella implant, while Charnley and Hutter illustrate two types of femur and tibia implant approaches in a total knee reconstruction. By contrast, the present invention is concerned with reconstructing a structure to take the place of an anterior cruciate ligament which has been separated from femur, as often happens to athletes. The present invention teaches a device with the particular ability to allow the surgeon to fix the exit point of a bony tunnel inside of the intercondylar notch as a landmark, with relative ease.

Applicant is also aware of certain drill guides which have been specially configured for orthopedic reconstructions of the hip, and particularly drill guides with particular utility for repairing fractures of the femoral neck. For example, the Great Britain patent illustrates one type of clamping device which assists in the repair of an intracapsular fracture of the femoral neck, wherein the drill bit is stopped from proceeding past the bone.

The patent to Schultz illustrates a non-analogous nailing device, wherein the clamp portion is placed around the femur in a manner whereby the lesser trochanter is usable as a reference point for nailing.

The patent to Deyerle teaches another approach to a total hip, wherein he employs a drill jig to assist in the fixation of a prosthesis head member, and also in drilling of the femur.

The patent to Neufeld is enclosed simply to illustrate a tubular drill guide, without any centering ability, and which requires fluoroscopy to locate the pin during a hip implant. The patent to Kronner illustrates a hip pinning tool which clamps directly on the femoral shaft to provide an immobile base, so that his alignment requires only an initial X-ray, and further adjustments being accomplished through calibrations about the axes D, E and along axis C.

The Shen design patent illustrates an ornamental device for an unrelated type of drill guide. The patent to McGuire illustrates a general purpose surgical clamp for holding two bones together, and particularly during a shoulder repair. Finally, the patent to Jaquet illustrates a general purpose device for treating bone fractures, wherein fixation pins can be set and pulled together by moving a screw, 26.

The present invention is particularly configured to allow the surgeon a ready and efficient manner for locating the exit of a bony tunnel within the intercondylar notch, and for this purpose the present invention provides for special relationships for the reconstruction of an anterior cruciate ligament, for example. None of the prior art has approached the special problems inherent in the creation of a bony tunnel in the distal end of the femur for this purpose, as will be more apparent from the following description of the preferred embodiment.

SUMMARY OF THE INVENTION

One of the most exacting aspects of the technique involved in the reconstruction of the anterior cruciate ligament is proper drilling of the bony tunnel, either through the lateral femoral condyle obliquely to, or from, the epicondylar region of the lateral femoral condyle transversely, toward the anatomical insertion of the anterior cruciate ligament in the femoral intercondylar notch. Accurate placement of the reconstructed cruciate ligament in its anatomical position cannot be overemphasized. It should be as far posteriorly as possible on the medial aspect of the lateral femoral condyle, in order to ensure the biomechanical competence of the reconstructed anterior cruciate ligament. Often times, the drilling of a hole through the lateral femoral condyle results in an exit in the intercondylar notch, which is far anterior than the surgeon intended. Accordingly, the mechanical efficiency of the reconstruction is compromised. According to my abovenoted technique, I have been able to demonstrate this problem by incorporating a cardiac pace-maker wire within the semitendenosis tendon as a marker. There has existed a need for a guide to ensure that this drilling is accurate, and to this point the only cruciate ligament guide known to me is the above-noted Marcus Stewart cruciate ligament guide, which is primarily configured for the attachment of a repairable torn anterior cruciate ligament, directly to its original femoral insertion. This particular guide is not readily adaptable for a reconstruction of an anterior cruciate ligament, wherein a large bony tunnel through the lateral femoral condyle is required for passage of the reconstructive material.

The present invention is considered to solve an acute need for an expedient cruciate ligament guide, and one which facilitates the most time-consuming part of my previously-discussed reconstructive procedure for the anterior cruciate ligament.

The present cruciate ligament drill guide has been shown to ensure accurate location of the bony tunnel, and it is believed that the present drill guide will enable the average orthopedic surgeon to make an anterior cruciate ligament reconstruction, and with greater ease than was heretofore possible.

An instrument according to the present invention includes dimensions which have been derived from actual in vivo measurement of both male and female patients, with weight ranging from 138 pounds to 216 pounds. The average dimension of the knee joint from the mid-point of the infra-patella tendon to the lateral epicondyle of the femur, with the knee in 90° flexion, is on the average of two inches, and in the range of one-and-a-half to two inches. (3.8 cm.–5 cm.) The average anterior posterior dimension, as determined from the anterior aspect of the infra-patellay tendon, to a point approximately one centimeter posterior and one-half centimeter inferior from the lateral femoral epicondyle is two-and-a-half inches (6.3 cm.) with an expectable range of two-and-a-quarter to two-and-three-quarter inches. (5.6 cm.–7 cm.) The 1.0 cm. posterior, and 0.5 cm. inferior location, with respect to the lateral epicondylar, region, is chosen as a landmark because this is the area of the femoral insertion of the anterior cruciate ligament, when projected on the lateral femoral condyle. Further understanding of these anatomy references can be had from the previously-discussed teachings of Girgis, et al.

Accordingly, it is an object of the present invention to quickly and accurately locate the outlet of a bony tunnel within the intercondylar notch, so that the mechanical competence of the resulting reconstruction will be maximized. The present drill guide includes a drill sheath at either end of a pair of vertically extending uprights, with an interconnection device so that the device can be clamped into exact placement by the surgeon, prior to drilling.

This surgical tool is adapted to be temporarily mounted to the distal end of the femur, in order to allow drilling of a required bony canal with a minimal amount of lost time and a maximum amount of accuracy. Accordingly to the preferred embodiment of the invention, a drilling through the femoral condyle is accomplished by a tool which essentially comprises a first longitudinally extending upright and a second longitudinally extending upright, wherein the distal ends of each upright include drill sheaths. The first upright and second upright are interconnected, at their proximate ends, through a mounting means which allows for transverse movement between the uprights. Each of the uprights are also movable in the longitudinal, or vertical, direction, since the first upright is slideable with respect to a first clamp assembly, and the second is slideable with respect to a second clamp assembly.

The mounting means which adjustably interconnects the first and second clamp assemblies further includes a guide bar extending between the two clamp assemblies, and the means to fix a clamp assembly upon the guide bar, and also to exert an exact amount of transverse compression. The means to contract the clamp assemblies, along the guide bar, is preferably a threaded screw which is threadably engaged into the first clamp assembly. This threaded screw is freely extending through the second clamp assembly, and includes a screw outer housing which rotatably surrounds the screw in the region of the second clamp assembly. Accordingly, a quick transverse adjustment of the device may be made by sliding and fixing the second clamp assembly upon this outer screw thread housing. Thereafter, further fine transverse adjustments can be made by rotating the threaded screw to transversely contract one clamp assembly with respect to the other.

Accordingly, the present invention allows the two drill sheaths to be both quickly moved, in either the vertical or transverse direction. This adjustability enables the surgeon to insert the second drill sheath into the intercondylar notch, and be assured that when drilling extra-articularly, through the first drill sheath, the exit of the bony tunnel created will be exactly at the correct anatomical femoral insertion of the anterior cruciate ligament.

The primary object of the present invention is to teach a drill guide which enables accurate exit location of a bony tunnel, drilled from outside, and quick adjustment to compensate for various anatomical variations in sizes of the distal end of the femur. It should be appreciated that while the preferred embodiment is shown used according to a process that illustrates my previously-discussed process for reconstructing the anterior cruciate ligament, other related applications are suggested by the present teachings of a device.

For further appreciation of the objects and advantages of the present invention, there now follows a detailed description of a preferred embodiment, wherein reference is made to the accompanying drawing.

BRIEF DESCRIPTION OF THE DRAWING

The drawing FIGURE illustrates a preferred embodiment of an anterior cruciate drill guide, being employed for its intended purpose in drilling of a bony tunnel through the lateral femoral condyle.

DETAILED DESCRIPTION OF THE PREFERRED EMBODIMENT

The drawing FIGURE illustrates application of the preferred embodiment of a drill guide according to the present invention. The tool comprises a first vertically extending upright, 2, and a second vertically extending upright, 4, wherein the distal ends of each upright include a drill sheath. The drill sheath, 8, located at the distal end of the first upright, is of a transversely elongated dimension, and it is shown with a drill bit, 36, entering in the transverse direction. The second vertically extending upright includes a smaller drill sheath, 6, at its distal end, since this drill sheath is intended merely to accept the tip of the drill bit, 36, as primarily guided by the elongated drill sheath, 8. The second drill sheath may be referred to as the intra-articular drill sheath, and the first drill sheath, 8, may also be referred to as the extra-articular drill sheath, in view of the utility shown in the drawing.

Each of these uprights are adjustable and moveable in a vertical direction, since they are each slideable within clamp assemblies. The first clamp assembly, 14, is slideable upon the first upright, and can be fixed by a holding device. A knurled set screw, 18, is an effective holding device, as would be other equivalent structure. The second clamp assembly, 16, is similarly mounted to allow the second upright, 4, to be located at any particular orientation, and fixed at that orientation by a knurled set screw, 20. It should be noted at this point that while each of the two uprights are capable of separate adjustment, it has been found that an initial adjustment is easily made by employing a rod (not shown) which is inserted through each of the drill sheaths, after the fashion in which the drill bit 36 is inserted. In this manner, an exact parallel relationship of the drill sheaths is initially assured, and then fixed by simply tightening the respective set screws, 18 and 20. Thereafter, transverse movement of the two uprights is accomplished by a mounting means, which will now be more particularly described.

The mounting means adjustably interconnects the first and second clamp assemblies, in order to allow a quick and accurate transverse movement of the two uprights, which have first been fixed in vertical positions. The drawing FIGURE shows a preferred mounting means for adjustably interconnecting the first and second clamp assemblies, and a mounting means which comprises a guide bar, 32, to extend between the respective clamp assemblies, 14 and 16. The guide bar, 32, may be fixed with respect to either one of the clamp assemblies, and in the preferred embodiment the guide bar is fixed to the second clamp assembly, 16.

An initial or rough transverse orientation of the two drill sheaths can be accomplished by setting one of two set screws, 10 and 12. The first clamp assembly, 14, includes a set screw, 10, which engages against the cylindrical outer screw housing, 22. This housing, 22, has transversely within it a threaded screw, 26, which can be rotated by a knurled knob, 24. There is a bore, 30, within the second housing which enables rapid sliding of the outer threaded screw housing, 22, prior to a clamping with the set screw, 10. The first clamp assembly has a threaded bore, 28, so that rotation of the knurled knob 24 will compress or extend, in a transverse direction, the distance between the two drill sheaths located at the distal ends of the two uprights. The screw 26 is meant as a fine adjusting compression device, following a rapid placement of the two vertical uprights through an initial adjustment of the set screw, 10, upon the screw housing.

As should now be apparent from the drawing FIGURE, the shorter drill sheath, 6, is applied intra-articularly to the anatomical insertion of the anterior cruciate ligament, with the longer sheath, 8, adapted to be inserted through the skin, and over the lateral epicondylar region. The transverse length of the second drill sheath guide, 6, is approximately 0.7 cm., and the transverse length of the first drill sheath, 8, is preferably approximately 3.3 cm., to ensure proper alignment. Each of the uprights, 2 and 4, are approximately 15 cm. in length, in the preferred embodiment, and the helical compression screw, 26, is approximately 20 cm. in length, from the knurled knob, 24, to its distal end.

According to my previously-noted reconstructive technique for an anterior cruciate ligament, a bony tunnel of approximately 0.64 cm. is required, and I found if the drill sheaths have respective outer diameters of approximately 0.9 cm., and clearance holes within of slightly more than 0.64 cm., there is effective guiding of a drill bit during use.

Further, in order to facilitate an exact immobile set upon transverse compression of the drill sheaths, each of the opposed faces of the drill sheath preferably include serrations, as shown at 34 and 48 in the drawing.

The drawing FIGURE shows a representation of a left knee 90° in flexion, with femur, 38, fibula 52 and tibial shaft, 50. The drawing FIGURE also shows a medial femoral condyle, 40, and a lateral femoral condyle, 42, with the intra-articular serrated drill sheath, 6, in position within an intracondylar notch, 44.

The drawing FIGURE also illustrates the transverse target line of a bony tunnel, 46, in a location which will be insured when the surgical drill guide is used as taught herein. It should be noted that the longer drill sheath, 8, is initially set in vertical relationship to the shorter drill sheath, 6, so that they line up in a parallel relation to the guide bar, 32. This is easily accomplished by simply inserting a rod which approximates the diameter of the drill, 36, through both of the drill sheaths, and then fixing the two screw clamps, 18 and 20, respectively. The pin is simply removed and the device may then be transversely adjusted so that after the intra-articular sheath, 6, is positioned, the extra-articular sheath, 8, can be positioned through simple transverse movement. The drill sheath, 8, slides transversely to an appropriate point, which may be either lateral epicondylar region, or supracondylar region of the femur, as decided following initial intra-articular placement of the drill sheath. Once the orientation is secure, the surgeon then tightens the set screw, 10, and makes his fine compression adjustment by turning the screw 26, with the knurled knob, 24. The projected serrations 48 are set to surround the exact landmark desired on the cruciate surface of the femoral condyle, to ensure accurate exit of the bony tunnel drilled. My reconstruction technique requires a drill of approximately 0.64 cm. diameter to accommodate the average semitendenosis tendon, including sheath. The present device drills an accurate hole sufficient for this purpose. Alternatively, the present jig can be used to perform the previously-discussed Hay-Groves method wherein the fascia lata is used to reconstruct an anterior cruciate ligament which has become disconnected from the femur.

While the FIGURE shows the instrument being used on a left knee, it is apparent that it is adaptable also to the right knee, simply by reversing the position shown.

While the preferred embodiment of the invention has been shown and described, it is to be understood that I intend the scope of my invention to be limited solely by the scope of the appended claims.

I claim:

1. A surgical tool adapted to be temporarily mounted to the distal end of a femur to allow precise drilling of a bony tunnel through a femoral condyle to a precise exit location on a femoral surface, said tool comprising:

a first longitudinally extending upright and a second longitudinally extending upright, with the distal end of the first upright including a first drill sheath and the distal end of the second upright including a second drill sheath, each of said sheaths defining a transversely extending guide for a drill, wherein each drill sheath has a serrated edge operable to fix the drill sheaths upon said condyle during a transverse contraction; and, first and second clamp assemblies, with said first and second uprights being respectively supported thereby, wherein said first upright is longitudinally slideable with respect to said first clamp assembly, and said second upright is longitudinally slideable with respect to said second clamp assembly; and, mounting means adjustably interconnecting said first and second clamp assemblies to allow a transverse relative movement between the clamp assemblies supporting said uprights, said mounting means further comprising a non-circular guide bar extending transversely between the respective clamp assemblies, and parallel to the drill guide defined by said sheaths and a screw means to transversely contract said clamp assemblies relative to each other, and upon said guide bar, whereby said second sheath can be placed within the intercondylar notch and said first and second sheaths can be transversely adjusted against a femoral condyle, wherein further said first drill sheath is sufficiently elongated in the transverse direction to accurately guide a drill bit that is inserted into said first drill sheath towards an exit point which is directly at the contact of said second drill sheath with said femoral surface.

2. A surgical tool according to claim 1, wherein said means for fixedly positioning each of said clamp assemblies further comprises a transversely extending helical screw which is threadably engaged into one of said clamp assemblies, and freely extending through the other of said clamp assemblies, wherein a screw outer housing rotatably surrounds said screw in the region of said other clamp assembly, whereby a quick transverse adjustment may be made by sliding and fixing said other clamp assembly upon said outer housing, wherein a further fine transverse adjustment is made by rotating said threaded screw to transversely contract said one clamp assembly with respect to said other clamp assembly.

3. A surgical tool according to claim 1, wherein the surgical tool further includes a removable shaft which is inserted through said first and second drill sheaths in order to longitudinally position said drill sheaths into an initial parallel relationship, with respect to said transversely extending guide bar.

4. A surgical tool according to claim 1, wherein each of said clamp assemblies are fixable upon said uprights by a threaded screw which respectively engages against each upright, and said one clamp assembly can be fixed against said transversely extending guide bar for an initial transverse positioning.

* * * * *